United States Patent [19]

Humphries

[11] Patent Number: 5,028,540
[45] Date of Patent: Jul. 2, 1991

[54] AVIAN IMMUNOGLOBULIN-PRODUCING CELL LINES

[75] Inventor: Eric H. Humphries, Dallas, Tex.

[73] Assignee: The Board of Regents, The University of Texas System, Austin, Tex.

[21] Appl. No.: 289,599

[22] Filed: Dec. 21, 1988

Related U.S. Application Data

[63] Continuation-in-part of Ser. No. 140,263, Dec. 31, 1987.

[51] Int. Cl.$^5$ .................. C12N 5/00; C12N 15/00; A61K 39/00
[52] U.S. Cl. .................. 435/240.2; 435/172.3; 435/240.1; 435/317.1; 435/948; 424/88; 935/111
[58] Field of Search .................. 435/240.27, 240.26, 435/240.2, 172.2, 172.3, 240.1, 240.2, 317.1, 948; 424/88; 935/111

[56] References Cited

OTHER PUBLICATIONS

Chen et al., Cell 31: 111–120 (1982).
Shay, in "Human Hybridomas and Monoclonal Antibodies", eds. Engleman et al., Plenum Press, New York, pp. 5, 12 (1985).
Roder et al., in "Human Hybridomas & Monoclonal Antibodies", eds. Engleman et al., Plenum Press, New York, pp. 55, 56 (1985).
International Search Report, PCT/US88/04680, May 19, 1989.
Barth et al., "A Nonimmunosuppressive Helper Virus Allows High Efficiency Induction of B Cell Lymphomas by Reticuloendotheliosis Virus Strain T," J. Exp. Med., vol. 167 (1988) 89–108.
Purchase et al., "A New Group of Oncogenic Viruses: Reticuloendotheliosis, Chick Syncytial, Duck Infectious Anemia, and Spleen Necrosis Viruses", J. Natl. Cancer Inst., vol. 51 (1973) 489–499.
Mussman et al., "Pathogenesis of Reticuloendothelial Virus Disease in Chicks—An Acute Runting Syndrome", Avian Dis., vol. 15 (1971) 483–502.
Olson, "Histopathologic and Hematologic Changes in Moribund Stages of Chicks Infected with T-Virus", Amer. J. Vet. Res., vol. 28 (1967) 1501–1507.
Hoelzer et al., "Transformation by Reticuloendotheliosis Virus: Development of a Focus Assay and Isolation of a Nontransforming Virus", Virology, vol. 93 (1979) 20–30.
Temin et al., "Replication of Reticuloendotheliosis Viruses in Cell Culture: Acute Infection", J. Virol., vol. 13 (1974) 291–297.

(List continued on next page.)

Primary Examiner—Elizabeth C. Weimar
Assistant Examiner—Jasemine C. Chambers
Attorney, Agent, or Firm—Arnold, White & Durkee

[57] ABSTRACT

The present invention involves a method for preparing antibody-producing chicken cell clones. This method comprises a series of steps including initially immunizing a first chicken with a desired antigen. A population of antibody-producing lymphocytes from bursa or spleen of the first chicken is separated.

The antibody-producing lymphocyte population is then infected with helper-free reticuloendotheliosis virus REV-T or helper-free reticuloendotheliosis virus REV-T and CSV (preferably REV-T(CSV)) and transplanted into a second chicken, the second chicken having been pretreated to remove normal B cells. The transplanted lymphocytes to proliferate in the second chicken, preferably for a period of at least about two weeks.

The lymphocytes from spleen, bursa or peripheral blood of the second chicken are isolated and plated out, for example in microtiter plates. Cell clones producing antibody such as IgG or IgM directed against the desired antigen are then selected. The isolation step most preferably involves cell culturing in the microtiter plates for a period of at least about one week.

25 Claims, 8 Drawing Sheets

Fig. 1
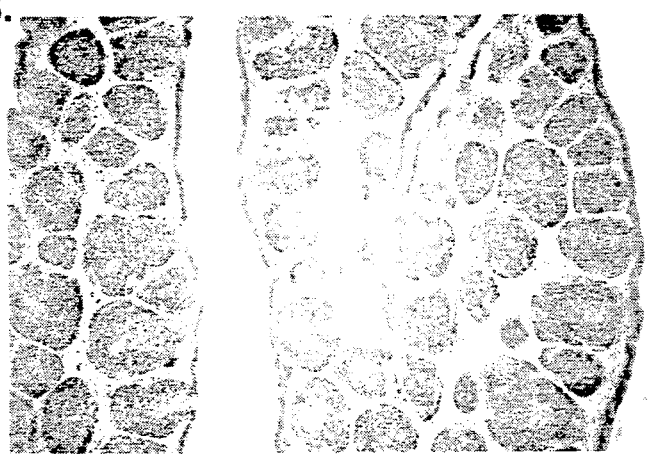
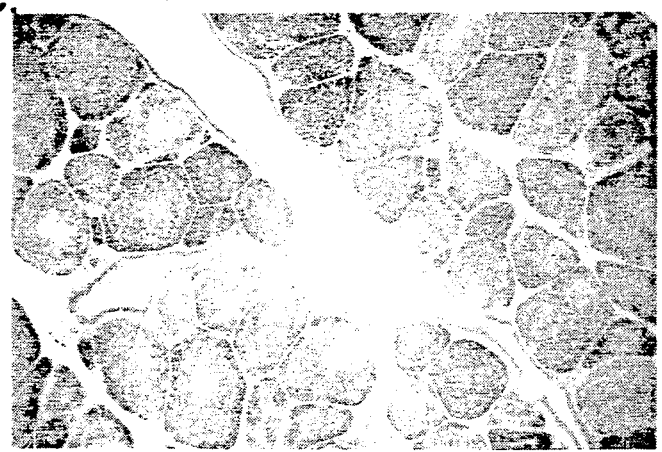

Fig. 1
D.
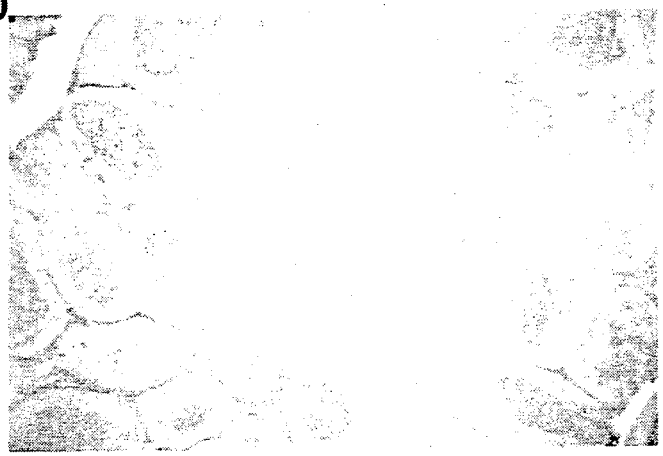
E.
F.

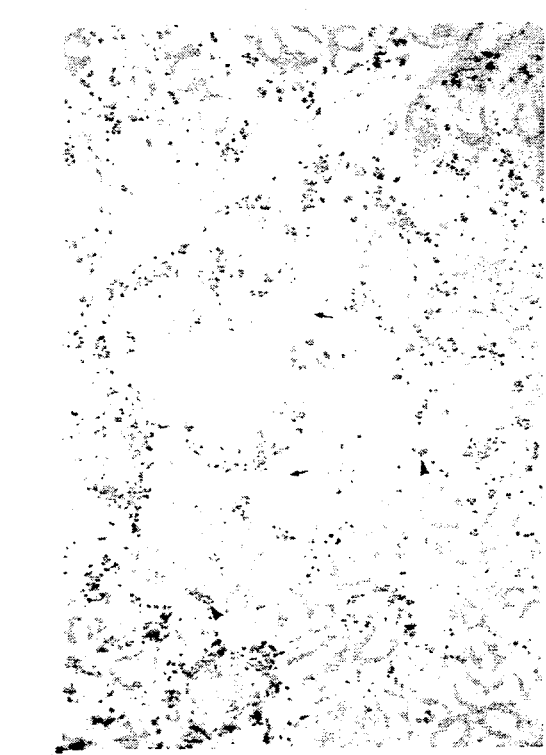
Fig. 2

Fig. 3
A.
B.
C.

Fig. 5
A.
B.
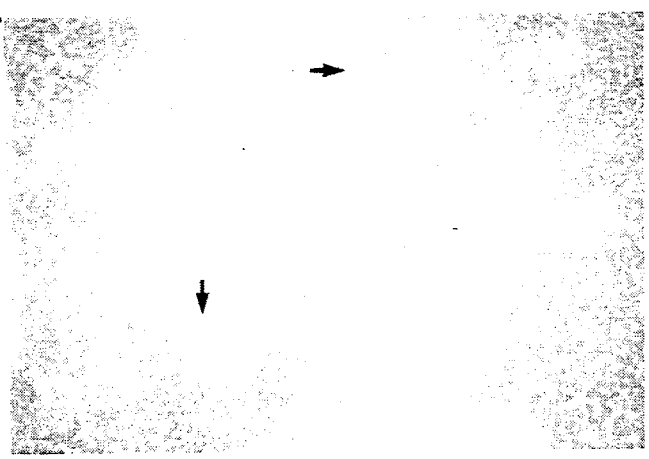
C.
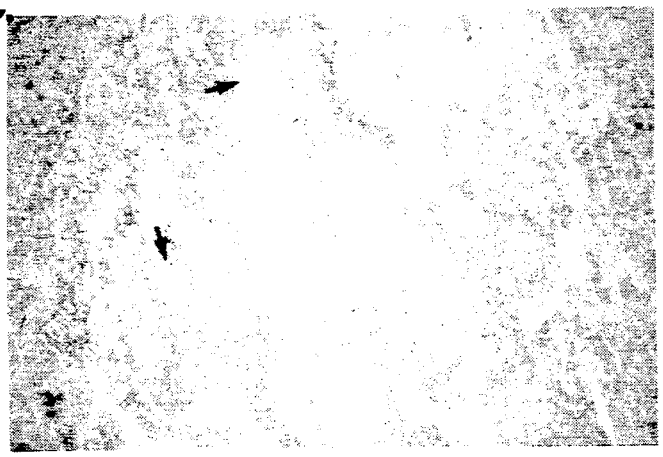

Fig. 5
D. 
E. 
F. 

AVIAN IMMUNOGLOBULIN-PRODUCING CELL LINES

Work relating to the present invention was partially supported by Public Health Service award CA41450 from the National Institutes of Health.

This is a continuation-in-part of U.S. patent application Ser. No. 07/140,263, filed Dec. 31, 1987 pending, allowed.

BACKGROUND OF THE INVENTION

Reticuloendotheliosis viruses (REVs) are a group of avian retroviruses that infect chickens, turkeys, and ducks (1). The prototype virus of this group is reticuloendotheliosis virus strain T(REV-T). REV-T(REV-A) designates a mixture of a replication-defective virus (REV-T) that induces acute neoplastic disease and a nondefective helper virus (REV-A) capable of inducing an immunosuppressive runting disease (2–4). REV-A and other non-defective REVs can be distinguished from REV-T by their ability to replicate in vitro in fibroblasts and their inability to induce acute neoplastic disease in vivo (5, 6). Some non-defective REVs, chick syncytial virus (CSV) and REV-A, induce a bursal-dependent B-cell lymphoma that is indistinguishable from avian leukosis virus (ALV)-induced lymphoid leukosis (6, 7). These tumors develop after a long latent period, are monoclonal and are characterized by proviral insertion within the c-myc locus (8, 9). In contrast, REV-T causes an acute neoplastic disease known as reticuloendotheliosis because the prominent cell in the original neoplastic lesion was morphologically identified as reticuloendothelial (10). These tumors develop rapidly, appear to be polyclonal and are thought to require the expression of the v-rel oncogene carried by REV-T (11, 12).

Despite the original description of the disease, the identity of the tumor induced by v-rel remains unclear. In situ characterization of the in vivo-derived tumor tissue has not been reported. In vitro studies suggest the REV-T-transformed cells are of early lymphoid origin (13, 14), but the absence of specific markers that define this phenotype has prevented conclusive identification. There are two reports of REV-T-derived cell lines which express IgM (14, 15) and it is possible that several phenotypically distinct cells may serve as target cells for v-rel-induced tumors.

REV-A is known to cause thymic and bursal atrophy as well as immunosuppression (2, 17, 18). Since the bursa is the major compartment of B lymphocyte development in the chicken, we reasoned that one consequence of REV-A infection and the subsequent disruption of this organ might be a reduction in B-cell proliferation and differentiation. If REV-T induces lymphoid tumors as suggested by studies of in vitro-derived REV-T cell lines, it is possible that REV-A replication influences the spectrum of lymphoid tumors that develop by reducing the pool of IgM positive B-lymphocytes that are available for REV-T infection. It has been reported that both immunosuppression and bursal atrophy are less severe in CSV-infected chicks (6, 18). We speculated, therefore, that if CSV provided the helper virus functions required for REV-T replication, the pool of cells available for infection by REV-T might contain significantly more IgM positive lymphocytes. Since IgM-positive tumor cell lines have been isolated following REV-T(REV-A) infection, albeit rarely, the present invention involves a prediction that REV-T(CSV) infection would lead to high frequency production of IgM positive B-cell lymphomas.

SUMMARY OF THE INVENTION

The present invention involves a method for preparing antibody-producing avian cell clones. This method generally comprises: immunizing a first bird with a desired antigen; separating a population of antibody-producing B-lymphocytes from the first bird; treating the antibody-producing B-lymphocyte population with v-rel under conditions inducing transformation; transplanting treated B-lymphocytes into a second bird, the second bird having been pretreated to remove normal B-lymphocytes, and allowing transformed B-lymphocytes to proliferate in the second bird; and isolating transformed B-lymphocytes from the second bird.

The isolating step may involve plating out said transformed B-lymphocytes and/or selecting cell clones producing antibody directed against the desired antigen. The isolating step may also involve panning said transformed B-lymphocytes on a solid surface comprising bound antibodies having binding specificity for the avian antibody being produced or its isotype.

The population of antibody-producing B-lymphocytes are usually separated from the bursa or spleen of the first bird. The isolation step is defined further as preferably involving cells from the spleen, bursa or peripheral blood of the second bird.

For purposes of practicing the method of the present invention, the v-rel oncogene is usually included in a reticuloendotheliosis virus, although transfection methods such as electroporation not involving virus may be used to transform B-lymphocytes.

In the general practice of the present invention, the birds are preferably chickens and the avian cell clones are chicken cell clones.

In greater particularity, the present invention involves a method for preparing antibody-producing avian cell clones comprising: immunizing a first bird preferably between about six weeks and two years of age, with a desired antigen, the immunization of the first bird being preferably monitored by routine serological analysis; separating a population of antibody-producing B-lymphocytes from the first bird; infecting the antibody-producing lymphocyte population with helper-free reticuloendotheliosis virus or reticuloendotheliosis virus and helper virus; transplanting the infected B-lymphocyte population into a second bird, the second bird being preferably between about one week and about sixteen weeks of age, and having been pretreated, for example with cyclophosphamide, to remove normal B-lymphocytes, and allowing the infected B-lymphocytes to proliferate in the second bird; and isolating infected B-lymphocytes from the second bird. The transplanted B-lymphocytes are generally allowed to proliferate for at least about two to three days in the second bird.

Again, the infected B-lymphocytes are isolated from the spleen, bursa, bone marrow, liver or peripheral blood of the second bird. The infected B-lymphocytes are isolated by a process involving plating out said isolated B-lymphocytes and selecting cell clones producing antibody directed against the desired antigen. The birds are preferably again chickens and the avian cell clones are chicken cell clones. The population of antibody-producing cells is preferably separated from the bursa or spleen of the first bird. The immunization of the first bird is indicated by measurement of an antibody titer of greater than about 1/200.

The methods of the present invention, in one embodiment, preferably involve the separation of antibody-producing B-lymphocytes by centrifugation in a density gradient comprising polysaccharide. The antibody produced by the methods of the present invention may be IgM, IgG or IgA, depending upon the lymphocytic cell types being transformed by v-rel. The isolation step of the present invention preferably involves plating cells out in microtiter plates in techniques well-known to those skilled in the arts. The methods of the present invention preferably use an isolation step involveing cell culturing in microtiter plates for a period of at least about one week.

In the processes of the present invention, the combination of helper-free reticuloendotheliosis virus and helper virus is designated REV-T(CSV) and the helper-free reticuloendotheliosis virus is REV-T. While the most preferred helper virus of the present invention is chick syncytial virus (CSV), the helper virus may also be spleen necrosis virus (SNV), attenuated REV-A or duck infectious anemia virus (DIAV). These helper viruses, which are nontoxic to B-lymphocytes, allow the incorporation of v-rel and resultant transformation thereby to facilitate creation of antibody-producing and long lived cell clones.

Another embodiment of the present invention involves a second method for preparing antibody-producing avian cell clones. The second method comprising a sequence of steps analogous in part to the methods described above. A bird is initially immunized with a desired antigen by the usual means. The bird is preferably a chicken and between about six weeks and two years of age. The immunization of the bird is preferably monitored by routine serological analysis, a proper immunization being indicated by measurement of an antibody titer greater than about 1/200.

A population of antibody-producing B-lymphocytes is then separated from said bird. 41. The antibody produced is preferably of an IgG, IgM or IgG isotype. The separating step may involve, for example, panning said antibody-producing B-lymphocytes on a solid surface comprising bound antibodies having binding specificity for avian IgM, IgG or IgA. This separation of antibody-producing B-lymphocytes may involve centrifugation in a density gradient comprising polysaccharide. This population of antibody-producing B-lymphocytes is preferably from bursa, spleen, bone marrow, gland of Harder, intestinal lining or peripheral blood of the bird.

The separated antibody-producing B-lymphocyte population is the treated with v-rel under conditions inducing transformation such as by transfection with or electroporation-induced entry of an agent containing a v-rel gene. The antibody-producing lymphocyte population may be treated, for example, with helper-free reticuloendotheliosis virus or reticulo-endotheliosis virus and helper virus to induce such cell transformation. The v-rel oncogene is characteristically included in a reticuloendotheliosis virus. The helper-free reticuloendotheliosis virus is preferablyt REV-T and the reticulo-endotheliosis virus with a helper virus is REV-T(CSV). The preferred helper virus is chick syncytial virus (CSV), although spleen necrosis virus (SNV), attenuated REV-A or duck infectious anemia virus (DIAV) may be used.

The treated B-lymphocyte population is then incubated in vitro under conditions facilitating proliferation of antibody-producing B-lymphocytes transformed by v-rel. This incubating step may comprise treatment of the treated B-lymphocyte population with the desired antigen and subsequent plating in microtiter plates. This step may also involve incubation of the treated B-lymphocyte population in culture medium comprising the desired antigen and/or B-cell mitogens. The B-cell mitogens may be one or more of lectins, cytokines and antibodies directed against B-lymphocyte surface protein.

A preferred additional step involving isolation of antibody-producing clones is often utilized. This final step characteristically involves plating out transformed B-lymphocytes following the incubating step. Such an isolating step involves selecting cell clones producing antibody directed against the desired antigen. Such a selection may be readily accomplished by a procedure involving panning said transformed B-lymphocytes on a solid surface comprising a bound second antibody having a specific binding specificity an avian antibody follows the incubating step.

BRIEF DESCRIPTION OF THE DRAWINGS

FIG. 1 shows a comparison of normal, REV-A, and CSV-infected bursal tissues. Bursal tissue from 2 week old normal, REV-A, and CSV-infected chicks was fixed in 10% neutral buffered formalin and processed for histological examination. Paraffin blocks were sectioned at 5 $\mu$m and slides were stained with hematoxylin-eosin (A, B, and C). Bursal tissue from 4 week old chicks was snap-frozen in 2-methylbutane at $-70°$ C. and sectioned at 8 $\mu$m. Slides were stained to reveal IgM expression using the PAP assay (D, E, and F). A and D) Normal bursa, B and E) REV-A-infected bursa, C and F) CSV-infected bursa.

FIG. 2 shows IgM expression in normal, REV-A, CSV, and ALV-infected splenic tissues. Spleens from 2 week old chicks were snap-frozen in 2-methylbutane at $-70°$ C. and sectioned at 8 $\mu$m. Slides were stained to reveal IgM expression using a PAP assay. A) Normal spleen, B) REV-A-infected spleen, C) CSV-infected spleen, and D) ALV-infected spleen. Arrows mark Schweigger-Seidel sheaths and arrowheads indicate plasma cells.

FIG. 3 shows expression of REV-A and CSV viral antigens in infected bursal tissue. Frozen sections of bursal tissue from 4 week old chicks were stained in a PAP assay with monoclonal antibody 11A25, which recognizes both REV-A and CSV antigens. A) Normal bursa, B) REV-A-infected bursa, and C) CSV-infected bursa.

FIG. 5 shows expression of IgM in REV-T(REV-A) and REV-T(CSV)-induced tumors. Adjacent serial sections of normal, REV-T(REV-A), and REV-T(CSV)-infected livers prepared from tissue frozen at 1 week post infection were stained (i) with hematoxylin-eosin or (ii) with an antiIgM monoclonal antibody. Hematoxylin-eosin stains of A) normal liver, B) REV-T(REV-A)-infected liver, and C) REV-T(CSV)-infected liver can be compared with PAP stains for IgM of D) normal liver, E) REV-T(REV-A)-infected liver, and F) REV-T(CSV)-infected liver. Arrows indicate non-tumor markers that allow correct orientation of the adjacent sections.

Figure 6:
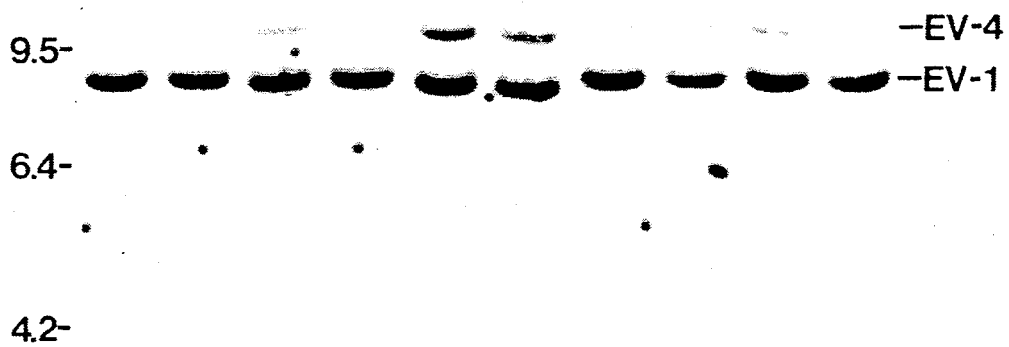

FIG. 6 shows analyses of the endogenous viral loci present in tumors isolated following transplantation of REV-T(CSV)-infected bursal lymphocytes. Cellular DNA was prepared from cell lines developed from tumors of cytoxan-treated birds repopulated with REV-T(CSV)-infected bursal lymphocytes. DNAs were digested with Eco RI and analyzed on 0.7% agarose gels, blotted to nitrocellulose, and hybridized with pBB-12 $^{32}$P-DNA in order to identify the endogenous viral loci present. Lanes 1) RBC DNA from a donor bird, 2) RBC DNA from a recipient bird, 3–10 DNAs from cell lines derived from tumors of a recipient bird. The cell lines were derived from liver nodules (lanes 3– 6), bursa (lane 7), thymus (lane 8), and spleen (lanes 9 and 10). Molecular weight markers are indicated in kilobases at the left and EV loci are designated at the right. The EV-4 fragment is 10 Kb and the EV-1 is 8.7 Kb.

Figure 7:

FIG. 7 shows analyses of v-rel sequences in tumors isolated following transplantation of REV-T(CSV)-infected bursal lymphocytes. Cellular DNA was prepared from cell lines developed from tumors of cytoxan-treated birds repopulated with REV-T(CSV)-infected bursal lymphocytes. DNAs were digested with Bgl II, analyzed on 0.7% agarose gels. After electrophoresis, DNA was blotted to nitro-cellulose and hybridized with pKW101 $^{32}$P-DNA in order to identify the REV-T integration sites. Lanes 1) RBC DNA from a donor bird, 2) RBC DNA from a recipient bird, 3–10) DNAs from cell lines derived from tumors of a recipient bird. The cell lines were derived from liver nodules (lanes 3–6), bursa (lane 7), thymus (lane 8), and spleen (lanes 9 and 10). Molecular weight markers are indicated in kilobases at the left and REV-T specific integration sites are marked with asterisks (*). Sizes of REV-T specific integration fragments range from >23 Kb to 3.7 Kb. c-rel fragments are 15, 9, and 6 Kb and are indicated with arrowheads at the right.

DESCRIPTION OF THE PREFERRED EMBODIMENT

The present invention involves a method for preparing antibody-producing chicken cell clones. This method comprises a series of steps including initially immunizing a first chicken with a desired antigen. A population of antibody-producing lymphocytes from the bursa or spleen of the first chicken is separated. The separation of antibody-producing lymphocytes preferably involves centrifugation in a density gradient comprising a polysaccharide such as FICOLL (Pharmacia). Additionally, the purification may involve binding of specific lymphocyte populations by employment of specific monoclonal antibodies in a panning procedure.

The first chicken is preferably between about six and eight weeks of age. The immunization status of the first chicken is determined by routine serological analysis, for example, by measurement of an antibody titer of greater than about 1/200. The antibody-producing lymphocyte population is then infected with either helper-free reticuloendotheliosis virus [REV-T] or reticuloendotheliosis virus and the helper virus chick syncytial virus CSV (designated REV-T(CSV)) and transplanted into a second chicken, the second chicken having been pretreated to remove normal B cells. The population of infected lymphocytes might be prepared by infection of the cells with REV-T prepared with either CSV or other helper viruses such as duck infectious anemia virus "DIAV" attenuated REV-A or spleen necrosis virus "SNV" (1). The transplanted lymphocytes are permitted to proliferate in the second chicken, preferably for a period of at least at least about two to three days.

The second chicken is preferably between about six and eight weeks of age and is pretreated with cyclophosphamide to remove normal B cells. The lymphocytes from spleen, bursa or peripheral blood of the second chicken are isolated and plated out, for example in microtiter plates. Cell clones producing antibody such as IgG, IgA or IgM directed against the desired antigen are then selected. The isolation step most preferably involves cell culturing in the microtiter plates for a period of at least about one week.

CELLS AND VIRUSES

SC chicken embryo fibroblasts (CEF) were cultured in plastic dishes (Nunc, Denmark) in $ET_{10}Ca_{10}$ [Dulbecco's modified Eagle's medium (DMEM, Flow Laboratories, McLeon, VA) containing 10% tryptose phosphate broth and 10% calf serum (Hazelton, Lenexa, KA) with antibiotics].

REV-A was rescued by calcium phosphate transfection of CEF with pSW253 provided by Dr. H. Temin (12). Transfected cells were cultured and transferred twice. Medium was harvested at 3 hour intervals from confluent plates, clarified by centrifugation at 250×g, passed through a 0.2 μm Nalgene filter, and stored at −70° C.

CSV(CN19691)-infected line 0 cells were provided by Dr. R. L. Witter. Culture medium from these cells was used to infect SC CEF and CSV stocks were prepared as for REV-A.

A REV-T nonproducer cell line developed in the laboratory of Dr. H. Bose by in vitro infection of spleen cells (14) was grown in $ET_{10}Ca_{10}$ $Ck_2$ [$ET_{10}Ca_{10}$ plus 2% chick serum (GIBCO, Grand Island, N.Y.)]. Stocks of REV-T(CSV) were made by infecting the REV-T nonproducer line with CSV and harvesting virus as above after several cell transfers.

REV-T(REV-A) was harvested from a clone of the bone marrow cell line isolated in the laboratory of Dr. H. Bose (19).

The REV-T(REV-A) described herein can be obtained from the American Type Culture Collection as ATCC VR-770 (strain T).

The REV-A described herein can be obtained from REV-T(REV-A) by end-point dilution to isolate infectious REV-A free of REV-T using techniques known to one skilled in the art and as described (4).

The CSV described herein can be obtained from the American Type Culture Collection as ATCC VR-588 (strain 9437).

The REV-T(CSV) described herein can be prepared by using REV-T(REV-A) to isolate a non-producer REV-T-transformed chicken cell line using techniques known to one skilled in the art and as described (14). The isolated non-producer REV-T-transformed cell line is then infected with CSV to produce cells that release REV-T(CSV).

Chickens and virus infections

Embryonated SC eggs were purchased from Hyline International Hatcheries, West Des Moines, Iowa and incubated with humidity at 39° C. On day 1 after hatch, chicks were infected via intrajugular injection with $10^5$ IU of REV-A, CSV, or REV-T per bird. The chicks were housed by the Animal Resource Center, University of Texas Health Science Center at Dallas, in rooms isolated from control or avian leukosis virus-infected chicks. CSV and REV-A-infected chicks were housed in separate cages in the same isolation unit. Food and water were provided ad lib. For repopulation studies, recipient chicks were injected intraperitoneally with 3 mg Cytoxan (cyclophosphamide, Mead Johnson, Syracuse, N.Y.) daily for 4 days after hatching to eliminate the resident B-cells (20). On the sixth day post hatch, sibling donor chicks were sacrificed by cervical displacement and their bursae were surgically removed. Bursae were then rinsed in DMEM plus antibiotics and minced with scissors. A single cell suspension which was >95% positive for Ig expression was prepared from bursal pieces and washed once with medium before resuspension in 2 ml of REV-T(CSV) per $5 \times 10^7$ cells (moi of 0.05 for REV-T). Cells were incubated with virus for 15 min on ice followed by 45 min at 37° C. to permit virus absorption and penetration. After one wash with medium, $5 \times 10^6$ of the infected bursal cells were injected via the jugular vein into cytoxan-treated recipients.

Sample Collection

Hematocrit samples were obtained from the wing vein and plasma was collected from the jugular vein and prepared as previously described (21). After sacrifice, the bursa, spleen, liver, and heart were excised and weighed as whole organs. The uppermost bilateral lobes of the kidney and 7 lobes of the thymus were excised for weighing in lieu of the total organs since complete recovery of these organs is difficult and prone to error. After the organs were weighed, samples for histology were fixed in 10% neutral buffered formalin and samples for immunohistochemistry were snap-frozen in 2-methylbutane at −70° C.

Cell line Isolation

Cell lines were isolated by preparing single cell suspensions from nodules in the liver and random sections of tissue from the spleen, thymus, and bursa. These suspensions were diluted into Hahn's medium (22) and cultured at 37° with 10% $CO_2$ for 48 hrs before transferring cultures at a 1:5 dilution into $ET_{10}Ca_{10}Ck_2$. Spleen and liver cultures were transferred at a 1:10 dilution every 24 to 48 hours thereafter. Bursa and thymus cultures required more time before the initial transfer; however, after the second or third transfer, these lines also required daily transfer. Liver suspensions were tested at the initial isolation for IgM expression by immunofluorescence, and all lines were assayed by the fourth or fifth transfer. Cellular DNA was isolated by the sixth cell transfer.

Virus Titrations

REV-A and CSV stocks were titrated by endpoint dilution onto SC CEF cultures as described previously (21). The REV-A titer was $2 \times 10^6$ IU/ml and the CSV titer was $1.5 \times 10^6$ IU/ml. We have experienced difficulty in establishing a reliable and quantitative in vitro assay for REV-T using standard methods (4). The titer of infectious REV-T relative to the infectious titer of REV-A or CSV was determined by comparing the amount of REV-T RNA with that of the helper virus. Viral RNAs were measured by hybridization to $^{32}$P-pKW101 (v-rel) and $^{32}$P-pSW253 (REV-A). Specific activities and the size of the probes were taken into consideration. In the REV-T(REV-A) stock, the titer of REV-A was $1.5 \times 10^4$ IU/ml, while the relative titer of REV-T was $8 \times 10^4$ IU/ml. In the REV-T(CSV) stock, the titer of CSV was $5 \times 10^5$ IU/ml, while the relative titer of REV-T was $1 \times 10^5$ IU/ml.

Infectious virus present in the plasma samples of infected chicks was also titrated by endpoint dilution onto SC CEF cultures. The reverse transciptase reaction used in this assay has been described by Waite and Allen (23).

Immunohistochemical Analysis

Antibodies used to distinguish between REV-A and CSV infection were obtained from Dr. R. L. Witter (24). The REV-A specific monoclonal antibody, llC100, was used at a final dilution of 1:400, whereas the monoclonal antibody capable of detecting both REV-A and CSV, 11A25, was used at a final dilution of 1:200. Monoclonal antibodies Hy-19 and Hy-16, which detect chicken IgM heavy chain and chicken IgG, respectively, were developed in this laboratory.

Cells used in indirect immunofluoresence assays were washed twice in 10 mM PO4, 150 mM NaCl, pH 7.5 (PBS) and resuspended to approximately $10^6$ cells/ml. To prepare cytospins, $10^5$ cells were centrifuged at $90 \times g$ and were fixed briefly in acetone before adding either Hy-19 or Hy-16 as primary antibody. Slides were incubated at 4° C. overnight, washed 3 times in cold PBS, and wiped dry before adding fluorescein-labeled goat anti-mouse IgG (Kirkegaard & Perry Laboratories, Inc., Gaithersburg, Md.). After a 90 minute incubation at 4° C., slides were washed 3 times in cold PBS, mounted in buffered glycerol, and examined by fluorescence microscopy. Frozen tissue was embedded in OCT medium (Lab-Tek Products, Naperville, Ill.) and sectioned on a cryostat at 8 μm. Sections were dried and fixed in ice cold acetone for 5–10 minutes. Once dried, slides were stored at −20° C. until use.

Acetone-fixed frozen tissue sections were stained with Hy-19 and Hy-16 using a peroxidase anti-peroxidase (PAP) technique. Tissues were blocked with 50% FCS in PBS containing 0.2% sodium azide and an equal volume of primary antibody was added. After a 30 minute room temperature (RT) incubation, the slides were washed in 20 mM Tris, 140 mM NaCl, pH 7.5 (TBS) 3 times for 5 minutes each at RT. After a brief fixation in 10% neutral buffered formalin, rabbit anti-mouse antibody (Dakopatts, Santa Barbara, Calif.) was added for a 20 minute incubation. After 3 TBS washes, monoclonal mouse PAP (Dakopatts) was added for another 20 minutes. After 3 TBS washes, the slides were developed in 3% ammonium acetate, pH 5.5 containing 450 μg/ml diaminobenzidine (Sigma, St. Louis, Mo.) and 0.0045% $H_2O_2$. Slides were dried, mounted, and examined by light microscopy.

Histology

Formalin-fixed samples were embedded in paraffin for histological examination and sectioned on a microtome at 5 μm. Transformed follicles were identified as described previously (25) except that bursae were serially sectioned at 200 μm intervals throughout the entire organ and stained with methyl green pyronin (Sigma) under conditions specified by the manufacturer. Hematoxylin-eosin staining was provided by the university pathology laboratory.

Analysis of cellular DNA

Cellular DNA was prepared from red blood cells or cultured cell lines derived from tumors as previously described (21). Eco RI and Bgl II enzymes were purchased from Boehringer Mannheim, Indianapolis, Ind. Digestion conditions were as specified by the manufacturer. Analysis of DNA by Southern transfer and hybridization conditions have been previously described (21). pBB12, a plasmid containing a 1300 bp fragment of gag sequences derived from the Schmidt-Ruppin A strain of avian sarcoma virus (26) was utilized to locate endogenous viral sequences. pKW101, a plasmid containing the 967 bp Eco RI fragment of v-rel sequences (27) was provided by Dr. H. Temin and utilized to locate REV-T-specific integration sites and c-rel sequences.

The present invention relates to the following results involving the earlier-described materials and methods.

ANALYSIS OF REV-A AND CSV INFECTION IN THE SC CHICK

Previous reports indicated that REV-A infection resulted in immunosuppression and bursal atrophy. Since CSV was reported to be less pathogenic than the other non-defective member of the reticuloendotheliosis virus family, we compared the effects of REV-A and CSV infection in the SC chick. One day old SC chicks were infected with $10^5$ IU of either REV-A or CSV. Hematocrits, organs and plasmas were collected from chicks at 1, 2, and 4 weeks after infection to examine the progression of disease. A comparison of total body weights indicated that REV-A-infected chicks were runted relative to control chicks. The comparative data are shown in Table I.

TABLE I

| COMPARISON OF REV-A AND CSV-INFECTED CHICKS* | | | | | | | | | |
|---|---|---|---|---|---|---|---|---|---|
| Time[a] | Birds[b] | Body Wt | Spleen | Liver | Bursa | Kidney | Heart | Thymus | Hematocrit |
| Uninfected | | | | | | | | | |
| 1 wk | 13 | 58 g | 0.08% | 3.6% | 0.33% | 0.31% | 0.81% | ND[c] | 37.5% |
| 2 wk | 9 | 103 g | 0.12% | 2.8% | 0.60% | 0.31% | 0.79% | ND | 33.4% |
| 4 wk | 7 | 241 g | 0.20% | 2.4% | 0.80% | 0.34% | 0.67% | 0.25% | 33.7% |
| REV-A-infected | | | | | | | | | |
| 1 wk | 5 | 54 g | 0.17% | 5.0% | 0.17% | 0.30% | 0.70% | ND | 31.5% |
| 2 wk | 9 | 71 g | 0.13%. | 3.7% | 0.21% | 0.30% | 0.58% | ND | 29.3% |
| 4 wk | 11 | 117 g | 0.15% | 3.9% | 0.22% | 0.29% | 0.57% | 0.15% | 18.0% |
| CSV-infected | | | | | | | | | |
| 1 wk | 4 | 64 g | 0.14% | 4.3% | 0.25% | 0.33% | 0.72% | ND | 33.5% |
| 2 wk | 10 | 94 g | 0.16% | 3.7% | 0.39% | 0.33% | 0.70% | ND | 34.3% |
| 4 wk | 7 | 187 g | 0.18% | 2.8% | 0.37% | 0.27% | 0.48% | 0.19% | 30.6% |

*SC chicks from Hyline were infected on day 1 after hatch with $10^5$ IU of REV-A or CSV via the jugular vein. Body weights are expressed as the average weight in grams. Organ weights are represented as the ratio of organ to body weight × 100. Hematocrits are averages of % packed cell volume.
[a]The time analysis was performed in weeks after infection.
[b]Number of birds analyzed.
[c]Not done.

While slight splenomegaly and hepatomegaly were observed, the bursa exhibited severe atrophy. By 4 weeks after infection, hematocrit values were low, indicating the presence of anemia in later stages of REV-A disease. These findings agreed well with previous observations of REV-A-induced runting, anemia, and bursal atrophy (2, 28). In contrast to REV-A infection, the consequences of CSV infection appeared relatively minor. Although atrophy of the bursa was detected, there was reduced runting and negligible anemia in the CSV-infected chick.

To further distinguish the effects of these two viruses on the bursa, sections of infected bursal tissue for histological and immunohistochemical analysis were prepared. Bursae from four birds infected with either REV-A or CSV were examined at 1 and 2 weeks after infection. Hematoxylin-eosin staining of the bursal follicles revealed that a majority (>80%) of the follicles in the REV-A-infected bursa were reduced in size (FIG. 1, A and B). Expansion of the interfollicular cell mass was evident throughout the organ. The cortico-medullary boundaries of the follicles were aberrant and individual cells appeared more eosinophilic and vaculolated with chromatin condensation at the nuclear membrane. This appearance is characteristic of dead or dying cells. In contrast, only a minority (<10%) of follicles in the CSV-infected bursa were similarly affected so that the tissue as a whole appeared nearly normal (FIG. 1 C). Bursae from several REV-A or CSV-infected chicks were stained to reveal IgM using the PAP assay (FIG. 1, D and E). The normal bursa was characterized by even staining throughout the tissue with more intense staining in the medulla. The anti-IgM staining pattern in REV-A-infected bursae was patchy and irregular with tissue from birds sacrificed 4 weeks after infection more obviously affected. In contrast, analysis of CSV-infected tissue revealed normal distribution of IgM in the bursa (FIG. 1 F).

As one of the functions of the bursa is to seed the spleen with IgM positive cells, the functional integrity of the bursa can be examined by determining the IgM staining pattern of the spleen. The PAP analysis, therefore, was extended to splenic tissue from normal, REV-A and CSV-infected 2 week old chicks. In control spleens, the B lymphocyte areas surrounding the Schweigger-Seidel sheaths stained positively for IgM while a few individual plasma cells stained intensely (FIG. 2 A). In contrast, CSV and ALV-infected spleens contained greater numbers of intensely staining plasma cells (FIG. 2, C and D). This increase in the number of plasma cells coincides with the appearance of an active immune response to virus (29, 30). Germinal centers were not observed as they require 3 to 4 weeks to develop. In distinct contrast to splenic tissue from ALV and CSV-infected chicks, REV-A-infected spleens exhibited an IgM staining pattern similar to that of uninfected birds (FIG. 2 B). The absence of an increase in intensely staining plasma cells in the REV-A-infected spleen coincided with the morphological atrophy of the bursa. Our results indicated that REV-A disrupts the ability of the bursa to seed the spleen with maturing plasma cells and that this immunosuppressive effect was distinct from the induction of suppressor T-cell activity that follows REV-A infection (17) and may be related to a diminished ability of REV-A-infected chicks to mount a humoral response against T-independent antigens (18).

HELPER VIRUS REPLICATION IN BURSAL LYMPHOCYTES

The differential effects of REV-A and CSV infection of bursal tissue might result from more extensive replication of REV-A in the SC chick. To evaluate this possibility, the amount of virus present in the plasma of REV-A and CSV-infected chicks was determined by end-point dilution. REV-A-infected birds maintained a viremia of $10^3$ to $10^4$ IU/ml of plasma throughout the 4 week time period examined, while CSV-infected chicks had 50 to 500-fold lower levels of virus circulating during the same period.

TABLE II

VIREMIA IN REV-A AND CSV-INFECTED CHICKS*

| Virus | Time | Birds | Average Viremia (IU/ml) |
|---|---|---|---|
| REV-A | 1 wk | 5 | $1.6 \times 10^4$ |
| | 2 wk | 9 | $1.6 \times 10^4$ |
| | 4 wk | 4 | $1.0 \times 10^3$ |
| CSV | 1 wk | 5 | $5.0 \times 10^2$ |
| | 2 wk | 10 | $4.0 \times 10^2$ |
| | 4 wk | 6 | $2.5 \times 10^0$ |

*One milliliter of blood was collected from REV-A and CSV-infected chicks at 1, 2, and 4 weeks post infection in 1 ml Alsever's solution to prevent clotting. Plasma was collected aseptically after centrifugation at 800 × g to remove cellular constituents and stored at −70° C. until use. Plasma samples were assayed for virus by end-point titration on SC CEF using the assay for reverse transcriptase as an indicator of virus replication. Viremias are expressed as averages in infectious units per ml.

These results indicate that REV-A infection leads to greater levels of circulating virus. To evaluate the extent of viral infection in the bursa, we employed monoclonal antibodies to assay frozen sections of bursal tissue for the presence of viral antigens. As expected, analysis with 11C1OO, specific for REV-A, detected antigen only in REV-A-infected tissue (data not shown). The analysis with 11A25, a reagent capable of reacting with both REV-A and CSV, demonstrated that both REV-A and CSV-infected tissue stained equally (FIG. 3). This result suggested that despite greater levels of circulating infectious REV-A, there is no difference in the amount of viral antigen present in bursal tissue infected with either virus and suggests that increased viral expression is not the basis for the toxic effect of REV-A on the bursa. However, a more detailed and quantitative analysis is necessary to substantiate this hypothesis which is not meant to limit the present invention but to clarify it by a possible mechanism.

VIRUS EXPRESSION IN THE TRANSFORMED FOLLICLE

Figure 4:
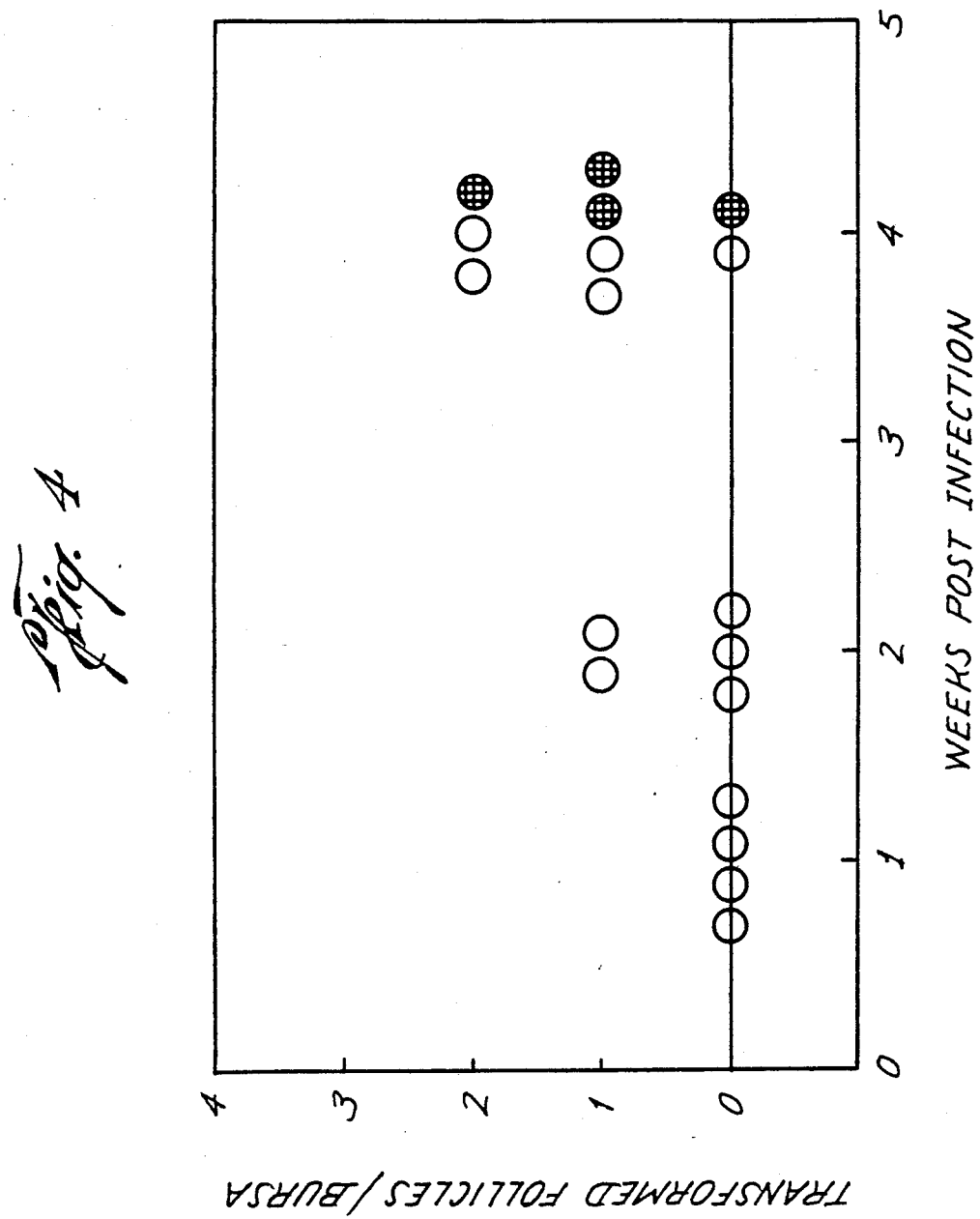
FIG. 4 shows incidence of transformed follicles in REV-A and CSV-infected chicks. SC chicks were infected with $10^5$ IU REV-A or CSV on day 1 after hatch and sacrificed at 1, 2, and 4 weeks post infection. Bursae were fixed in 10% neutral buffered formalin and processed for histological examination. Serial sections were prepared throughout the entire bursa at 200 $\mu$m intervals, stained with methyl green pyronin, and examined for the presence of transformed follicles. Each symbol represents the number of transformed follicles in a single bursa. Open symbols (0) represent CSV-infected bursae and closed symbols (◯) represent REV-A-infected bursae.

REV-A and CSV are known to cause lymphoid leukosis, a disease that is bursal-dependent and characterized by the early development of a preneoplastic lesion designated the transformed follicle (25). To examine the presence of transformed follicles in REV-A and CSV-infected bursae, formalin-fixed bursal tissue was serially sectioned and stained with methyl green pyronin. No more than two transformed follicles per bursa were observed in either REV-A or CSV-infected tissue (FIG. 4). Data from analysis of ALV-infected chicks suggests that the maximum number of transformed follicles were seen by 4 weeks after infection (25). Significantly, equivalent numbers of transformed follicles were seen in both infected tissues. This assay was repeated using frozen tissue sections and adjacent serial sections containing transformed follicles were stained by the PAP assay to detect the presence of viral antigens and IgM. Transformed follicles from both infected birds contained viral antigen, indicating that either REV-A or CSV replication can occur within proliferating bursal lymphocytes without resulting in cell death. Further, consistent with normal B-lymphocyte function, these transformed follicles exhibited IgM expression. Therefore, although REV-A infection resulted in either destruction or depletion of the bursal population, it seemed unlikely that this is a direct consequence of viral replication within bursal lymphocytes.

REV-A AND CSV AS HELPER VIRUSES FOR REV-T-INDUCED DISEASE

Having established the consequences of REV-A and CSV infection in the day old chick, these two viruses were compared as helper viruses for REV-T-mediated tumor induction. One day old SC chicks were infected with either REV-T(REV-A) or REV-T(CSV) and sacrificed at one week. Analysis of body and organ weights showed a significant increase in spleen and liver weights of birds infected with either REV-T(REV-A) or REV-T(CSV).

TABLE III

COMPARISON OF REV-T(REV-A) AND REV-T(CSV)-INFECTED SC CHICKS

| Birds | Body Wt | Spleen | Liver | Bursa | Kidney | Heart | Thymus | Hematocrit |
|---|---|---|---|---|---|---|---|---|
| Uninfected | | | | | | | | |
| 13 | 58 g | 0.08% | 3.6% | 0.33% | 0.31% | 0.81% | 0.17% | 37.5% |
| REV-T(REV-A)-infected | | | | | | | | |
| 13 | 54 g | 0.28% | 5.4% | 0.20% | 0.35% | 0.72% | 0.11% | 29.1% |
| REV-T(CSV)-infected | | | | | | | | |
| 10 | 56 g | 1.02% | 7.2% | 0.21% | 0.39% | 0.75% | 0.13% | 29.4% |

*SC chicks from Hyline were infected with REV-T(REV-A) or REV-T(CSV) on day 1 after hatch and were sacrificed 1 week later for analysis. Samples for hematocrits were obtained from the wing vein prior to sacrifice. Body weights are represented as the average weight in grams. Organ weights are expressed as the ratio of organ to body weight × 100. Hematocrits are averages of % packed cell volume.

This increase appeared to correlate with the tumor mass observed at autopsy. Moreover, REV-T(CSV)-infected spleens were significantly larger than those from REV-T(REV-A)-infected birds. There was no difference in the bursal weights between chicks infected with either virus; however, both were decreased in comparison to uninfected controls. Anemia was observed in chicks infected with either virus, suggesting tumor involvement in the bone marrow. The large increase in the size of REV-T(CSV)-infected spleen and liver suggested that tumor development resulted from REV-T infection of a population of cells that is not present, or at least less susceptible to infection and proliferation, in the REV-T(REV-A)-infected chicks. Spleen, liver, bursa, and thymus tissue from infected birds were analyzed for the presence of tumors. In order to detect the majority of tumors present in the affected organs, each tissue was serially sectioned in at least four distinct areas approximately 200 μm apart and examined with hematoxylin-eosin, methyl green pyronin, anti-IgM and anti-IgG staining. Six REV-T(REV-A) and four REV-T(CSV)-infected birds were analyzed. Due to the extensive range in size and number of tumors present in the affected organs, it was difficult to quantitate precisely the number of individual tumors per bird. However, the majority of tumors (~90%) identified by hematoxylin-eosin staining in the REV-T(REV-A)-infected liver were negative for IgM expression, whereas the majority of tumors (~90%) in the REV-T(CSV)-infected liver were positive for IgM expression (FIG. 5). While analysis of the spleen and bursa was more difficult due to the background of IgM positive cells in these organs, the same general observation was apparent. The number of tumors present in the thymus was too few to be informative. None of the tumors in any tissue were positive for IgG expression.

The difference between the phenotype of these two tumors was pursued by developing cell lines from tumor tissue. Twenty-seven cell lines were developed from tumors of 13 REV-T(REV-A)-infected birds and 16 cell lines were made from tumors of 9 REV-T(CSV)-infected birds. Lines derived from REV-T(REV-A)-induced tumors were never more than 30% positive for IgM expression, while lines derived from REV-T(CSV)-induced tumors were 50 to 100% positive for IgM expression.

TABLE IV

COMPARISON OF REV-T(REV-A) AND REV-T(CSV) TUMOR-DERIVED CELL LINES*

| Phenotype | Number of REV-T(REV-A) Lines | Number of REV-T(CSV) Lines |
|---|---|---|
| Uncloned | | |
| IgM − | 17 | 0 |
| 1–30% IgM + | 10 | 0 |
| 50–100% IgM + | 0 | 15 |
| Cloned | | |
| IgM − | 34 | 3 |
| IgM + | 0 | 29 |
| Total Birds[a] | 13 | 9 |
| Total Uncloned | 27 | 15 |
| Total Cloned | 34 | 32 |

*Tumor tissue from REV-T(REV-A) and REV-T(CSV)-infected birds were minced with scissors and cultured in Hahn's medium. Cultures were transferred at 1:5 or 1:10 dilutions 24 to 48 hours after the initial plating and passaged every 1 to 2 days thereafter. Cell lines were assayed for IgM expression after 4 or 5 transfers. Clones from these lines were established in soft agar and analyzed for IgM expression after amplification.
[a]The number of individual birds from which uncloned cell lines were derived.

Clones from these lines were established in soft agar and analyzed for IgM and IgG expression. Of 34 REV-T(REV-A)-generated clonal lines tested, all 34 were negative for IgM expression. In contrast, of the 32 REV-T(CSV)-induced clonal lines assayed, 29 were IgM-positive. All of the clones were negative for IgG expression. Therefore, the cell line analysis correlated well with the in vivo tumor analysis showing that REV-T(REV-A) infection induces primarily IgM-negative tumors while REV-T(CSV) infection induces primarily IgM-positive tumors.

THE REV-T(CSV)-DERIVED IgM POSITIVE TUMOR CELL CAN BE OF BURSAL ORIGIN

In the day old chick, the major population of proliferating B-cells is located within the bursa. Since REV-T(CSV) infection produced predominately IgM positive B-cell tumors, it was determined whether or not bursal lymphocytes could serve as target cells for REV-T-induced tumors. A bursal repopulation experiment was performed which utilized the segregating endogenous viral locus 4 (EV-4) of the SC chick as a marker to differentiate between donor and recipient cells (26). EV-4-negative chicks were used as recipients while EV-4 positive chicks were employed as donors Recipient SC chicks were treated with cytoxan and repopulated with CSV-infected donor bursal B cells. Five and a half days later, three morbid recipient birds were autopsied for the presence of tumors. For each bird, five separate tumor nodules from the liver, three separate portions of the spleen, and a portion each of bursa and thymus were removed to prepare cell suspensions for cell line development. A small sample of the liver suspension was assayed for IgM expression by immunofluorescence. In order to minimize selection, uncloned cell lines were analyzed between the 4th and 6th transfer following isolation for IgM expression, presence of EV loci, and viral integration. Analysis of the liver cell suspensions prepared at isolation showed that all samples were 50% to 100% positive for IgM. As the liver suspensions were prepared from tumor nodules and were probably clonal, the high percentage of IgM positive cells was expected. Cell lines grew out of all tissue samples taken, including the thymus preparations. When these lines were tested for IgM expression at the 4th transfer, all lines, whether derived from liver, spleen, bursa, or thymus, were greater than 99% IgM positive. This result demonstrated that IgM-positive tumor was present in all tissues and, therefore, capable of metastasis and proliferation in multiple microenvironments.

Because helper virus was present in REV-T(CSV), a spreading infection was established once the infected bursal cells divided following transplantation. Consequently, the DNA from the cell lines had to be analyzed for the EV-4 locus to positively identify the lines as being of donor origin. DNA samples digested with Eco RI were analyzed by Southern transfer and hybridization with pBB12 to detect EV loci. Eighteen cell lines from 2 birds were analyzed, along with donor and recipient RBC DNA. Of the 18 lines, 16 had EV-4 loci, demonstrating they were of donor cell origin (FIG. 6). This experiment demonstrates that REV-T is capable of infecting cells of bursal origin and inducing IgM positive tumors that appear at the time of tumor initiation to be both bursal-independent and capable of in vitro proliferation.

The cell lines were analyzed for unique REV-T integration sites to determine whether the tumors from which these lines were developed were identical. DNA was digested with Bgl II which cuts once inside REV-T but outside v-rel sequences (31). Bgl II digestion and hybridization to v-rel, therefore, identifies a single unique fragment for each exogenous REV-T integration. The pKW101 rel-specific probe used also hybridizes to three fragments of c-rel (32). When DNA samples from the tumor lines were analyzed for rel-specific sequences, integration specific bands were detected in every line (FIG. 7). The multiple bands observed in lines developed from bursal, thymic, and splenic tumor tissue probably represent multiple, independent tumors as these cell lines were not cloned. Consistent with this interpretation, the hybridization of v-rel to the integration specific fragments is less intense than to fragments of c-rel (which served as an internal standard for a single copy gene), indicating significant heterogeneity in the tumor population. Lines developed from liver nodules had single integration-specific fragments which hybridized with intensities equivalent to that of fragments of c-rel, indicating that these lines were probably clonal with respect to REV-T integration. Twenty seven different patterns of integration were found in 29 different lines isolated from 3 birds indicating that multiple REV-T-infected bursal B-lymphocytes gave rise to tumors in this system.

IN VITRO REV-T(CSV) TRANSFORMATION OF CHICKEN B-CELLS

The results from the in vivo studies described above were followed by an attempt to transform B-cells in vitro with REV-T(CSV). In vitro infection could be used directly to produce isolated clones of permanent B-cell lines secreting immunoglobulin. Cell suspensions were isolated from bursa, spleen, bone marrow and peripheral blood of 3 week old chicks. The cells were further purified by Ficoll gradient centrifugation. Preparations of these different mononuclear cells containing $10^8$ cells were infected for 30 minutes at 37° C. with approximately $1 \times 5$ infectious units of REV-T(CSV) and the cells seeded in Hahn's medium (22) in microtiter trays at $10^5$ cells per well. Four hundred wells were plated for each infected cell type including bursal, splenic, bone marrow and peripheral blood. The cells were incubated at 37° C. in $CO_2$ for seven to ten days. Wells that were positive for growth were expanded in standard growth medium as described above. In no case were more than 15% of the wells positive for growth. Each well positive for growth, therefore, could be considered in clonal in origin. These clonal outgrowths were then screened for immunoglobulin production. Forty-seven of 49 bursal clones were positive for IgM expression. Twenty-six of 40 splenic clones were positive for IgM expression. 5 of 12 bone marrow-derived clones and 3 of 9 peripheral blood-derived clones were positive for IgM expression. These results demonstrated that in vitro REV-T(CSV) infection of different mononuclear cell populations containing B-cell lymphocytes leads to clonal proliferation and isolation of immunoglobulin positive B-cell lines with high efficiency.

This in vitro procedure should work using any v-rel expressing virus including helper-free REV-T and REV-T packaged by other helper viruses such as DIAV, SNV or REV-A variants. The present results indicate that this procedure works even with REV-A as a helper virus, though less efficiently. This in vitro procedure should also be usable following electroporation or transfection of the v-rel gene into these different lymphocyte populations.

This method could be modified further to increase both efficiency and productivity by isolating isotype specific lymphocytes from various anatomical compartments, (e.g. bursa, spleen, gland of Harder, etc.). Folowing Ficoll gradient centrifugation, selective isolation of either IgM, IgA or IgG bearing lymphocytes prior to infection can be achieved by isotypic selective panning using alpha-IgM, alpha-IgA or alpha-IgG antibodies. This purification would enable preparation of greater numbers of clones bearing a given immunoglobulin isotype.

A modification of the above-described in vitro method should increase the efficiency with which clones producing antigen-specific immunoglobulin are isolated. In this modification, the REV-T-infected lymphocytes would be incubated in vitro in the presence of the antigen used to immunize the bird (from which the cells were isolated) prior to plating in Hahn's medium. alternatively, the antigen could be bound to the microtiter plates in which the cells are plated. This modification is based upon the concept that the antigen will act as a specific mitogen for the immunoglobulin positive cell expressing the antibody specificity for that antigen. Other molecules that would be mitogenic for these B-cells would also be added to stimulate growth and thereby initiate expression of v-rel. Included in the list of mitogens would be Bcell cytokines as well as antibodies against other cell surface markers such as Ia.

Certain aspects of the present invention may be discussed specifically as follows.

HIGH FREQUENCY INDUCTION OF IgM POSITIVE B-CELL LYMPHOMAS

Results relevant to the present invention and described herein demonstrate that by using chicken syncytial virus to provide the helper functions for REV-T replication, following infection of day old chicks, the majority of induced tumors express IgM. The tumors within a single bird were polyclonal, which suggested that initiation and tumor development occur efficiently within a number of cells. The present results also demonstrated that bursal B-cells infected by REV-T(CSV) were able to develop as a disseminated IgM positive tumor. Dissemination to a variety of microenvironments occurred without requiring an extended period of tumor progression, indicating that the initial tumor was bursal-independent. These same tumors proliferated indefinitely as in vitro cell lines. These experiments provide the first evidence that expression of v-rel can induce IgM positive B-cell tumors with a high efficiency. Previous studies characterizing in vitro-derived cell lines with a variety of heterosera, including several directed against both B and T lymphocytes of the chicken, have suggested that REV-T(REV-A) induces a poorly defined lymphoid tumor perhaps within the B-cell lineage (13–15). The issue of tumor phenotype is somewhat confused as the original tumor was described as reticuloendothelial perhaps within the macrophage-dendritic cell lineage (2, 3, 10). Definitive markers capable of identifying these tumors and relating their phenotype to that of a normal cellular compartment have not yet been identified. In retrospect, it is significant that two REV-T-induced cell lines expressing IgM have been isolated (14, 16). Our in situ analysis of tumors produced following infection with REV-T(REV-A) revealed that less than 10% of these tumors expressed IgM. None of the cell lines prepared from these tumors (isolated on a completely random basis) expressed IgM. While analysis of tumor tissue has not been reported, these results are consistent with previous in vitro observations (13–15). The observations described herein that altering the helper virus that provides the viral proteins for REV-T replication also changes the type of tumor induced by v-rel expression appears to be the first report of such a phenomenon. Other helper viruses are able to influence the course of tumor development following infection by an acute transforming retrovirus but the actual type of tumor that develops remains unchanged. The development of Abelson disease can be markedly influenced by the specific helper virus with which the animal is infected but only the incidence and rate of disease onset are altered (33). Similarly, the type of Friend disease is specified by the infecting strain of SFFV, either $SFFV_a$ or $SFFV_p$, as determined by the different env regions (34). In each instance, different strains of helper MuLV can influence the course of the disease. In contrast to these examples, REV-A and CSV have a direct influence on the actual type of tumor that REV-T induces. As discussed below, this influence appears related to the cytotoxic effect REV-A replication has on the IgM positive B-cell population within the bursa.

REV-A INDUCES EXTENSIVE BURSAL ATROPHY

Previous work has shown that REV-A induces the appearance of a suppressor T cell that correlates with a state of immunosuppression that is independent of bursal function (17, 18, 35). While the basis for this phenomenon has not been determined, it would appear to differ from the mechanism by which REV-A influences the spectrum of REV-T-induced tumors. The IgM negative tumor induced by REV-T(REV-A) appears to result from the generalized atrophy that affects the bursa. The present analyses of the bursa demonstrates not only that the size of the bursa was reduced but also that the tissue within this organ was disrupted and the expression of IgM aberrant. It may be relevant that acute REV-A infections were known to be cytotoxic to fibroblasts in vitro (5). The interfollicular tissue, a potential source of fibroblast and stromal cell-derived growth factors, was markedly altered. While there was no direct evidence, it seemed likely that the B-cell population, which normally undergoes extensive proliferation and differentiation, had ceased division and was stationary or dying. Under these conditions, while REV-T may be able to infect the bursal lymphocyte population, activation of v-rel expression and tumor induction would be unlikely. In contrast, while the bursa in the CSV-infected chick was smaller than in the uninfected chick, both the follicular structure and the cells within the follicles appear healthy and normal. It appeared that CSV enables REV-T to induce primarily IgM-positive tumors by not destroying the bursal lymphocyte and thereby enlarging the target cell population to include proliferating, maturing B-cells.

Further work will be required to elucidate the specific mechanism by which REV-A exerted its pathogenic effect on the bursa. It is significant, however, that both viruses appeared able to replicate with equal efficiency in bursal tissue as evidenced by the expression of viral antigen. Furthermore, the expression of REV-A antigens within bursal lymphocytes did not appear to be cytotoxic by itself as transformed follicles, equally frequent in both REV-A and CSV-infected chicks, express such proteins in roughly equal quantities. It also seemed unlikely that immune elimination of REV-A-infected tissue was responsible for atrophy of the bursa, since at the height of the humoral response during an ALV infection, ALV DNA sequences were eliminated rapidly from both the bone marrow and the peripheral white blood cell population while they were selectively maintained in the bursa (36). It appears likely that REV-A infection resulted in destruction of the bursal stroma such that stromallymphocyte interactions and/or production of essential growth factors required for B-cell proliferation and survival are absent. It was possible that one of the REV-A glycoproteins binds to bursal cells or a specific growth factor thereby blocking an interaction required for bursal lymphocyte proliferation. It has been proposed that a 26 amino acid peptide found in a number of retroviral transmembrane glycoproteins has immunosuppressive activity (37). A similar sequence has been located in gp20 for REV-A (38).

THE TARGET CELL AND V-REL-INDUCED NEOPLASTIC DISEASE

The observation that REV-T can induce tumors that are predominantly IgM-positive demonstrates that the spectrum of cells in which v-rel is able to induce neoplastic disease is larger than originally thought. While two IgM positive cell lines have been seen before, the fact that the frequency with which they can be induced is so dramatically altered by changing the helper virus illustrates that access to a given cell type plays a significant role in defining which cells are target cells for v-rel-induced tumorigenesis. While access to the IgM target cell may have been uniquely provided by the helper virus in this system, a formally similar situation has been studied with Abelson virus-induced disease. The range of cell phenotypes that can be transformed in vitro by A-MuLV includes pre-B, immature and mature B-lymphocytes, erythroid precursors, macrophages and mast cells (39–41). Not all of these cells however, serve as targets in vivo. Pre-B and immature B-lymphocytes serve as the most frequent target cells for Abelson-induced tumors (42, 43). In contrast, mast cells and macrophages serve as targets infrequently and Abelson-induced erythroid tumors have not been observed (39, 44). These data support the conclusion that a variety of factors beyond the ability of expressed v-abl sequences to function in a permissive environment are important in determining whether or not a cell serves as a target for Abelson-induced tumor development.

Defining the range of target cells has important implications for identifying the cellular genes that are involved in v-rel-mediated tumor development. Of particular interest to this laboratory is the genetic analysis of B-cell lymphoma development in the chicken. The IgM positive bursal-derived tumor induced by expression of v-rel differs significantly from the IgM positive bursal derived tumor isolated following ALV infection. This ALV-induced tumor is characterized by elevated levels of c-myc resulting from viral integration within the normal cellular locus (45, 46). While these two tumors have developed from apparently similar target cells and appear phenotypically identical, their development, as outlined in Table V, is quite distinct and indicates that significant differences exist in the genetic pathways utilized in the development of these two lymphomas.

TABLE V

COMPARISON OF REV-T(CSV) AND ALV-DERIVED IgM POSITIVE B-CELL LYMPHOMAS

| REV-T(CSV)-Induced | ALV-Induced |
| --- | --- |
| Develop within 1-2 weeks | Development requires 3-6 months |
| Apparent single hit kinetics | Multiple hit kinetics |
| No preneoplastic lesion | Indentifiable preneoplastic lesion |
| Primary tumor is bursal independent | Primary tumor is bursal dependent |
| Tumor progression not required for metastasis to non-bursal sites | Tumor progression required for metastasis to non-bursal sites |
| Adaptation to in vitro growth not required | Adaptation to in vitro growth required |

A molecular comparison of the sequences expressed in the two tumors should identify genes that function specifically in one or the other of the pathways thereby providing information that is important in dissecting the functions of v-rel and c-myc during neoplastic development in the avian B-lymphocyte.

The present invention involves the effects of both REV-A and CSV infection on bursal tissue. REV-A infection resulted in bursal atrophy, destroying both its structural and functional integrity. In contrast, the bursa in CSV-infected chicks, while reduced slightly in size, appeared both structurally and functionally normal. REV-A-induced bursal atrophy was not a result of viral replication in the B-lymphocyte as: (i) both viruses were capable of inducing, with equal efficiency, the formation of preneoplastic lesions containing proliferating B-lymphocytes; and, (ii) it appeared that equivalent amounts of viral antigen were expressed in the bursa of chicks infected with either virus.

In REV-T(REV-A)-infected chicks, the majority of tumors that developed were negative for IgM expression. In contrast the majority of tumors induced by REV-T(CSV) infection were IgM positive. This finding was confirmed by recovery of IgM negative cell lines from REV-T(REV-A)-infected chicks and IgM positive cell lines from REV-T(CSV)-infected chicks. In addition, repopulation studies showed that IgM-positive bursal-derived cells served as target cells for REV(CSV)-induced lymphomas. REV-T can induce IgM-positive B-cell lymphomas with high efficiency. Infections by the helper viruses, REV-A and CSV, differ dramatically in their effects on the composition of the population of cells that serve as targets for REV-T-induced neoplasia.

There are several advantages in using the chicken to produce monoclonal antibodies. At least four specific exemplary types of monoclonals isolated from the chicken would be significant value.

a) Many human antigens are not seen by the mouse because they are highly conserved between man and mouse. Since the chicken is phylogenetically more distant from man, a significant number of chickens monoclonals should be developed against important human antigens.

b) Many mouse antigens are traditionally recognized by allotypic heterosera. These antisera are frequently weak and difficult to produce. Other antigens, of course, have not been recognized because they are identical in the immunized mouse. Both sets of antigens would be excellent candidates for recognition by the chicken monoclonals.

c) Several important avian pathogens are of enormous economic significance. Defining the epitopes seen by the chicken during infection with these pathogens by using avian monoclonals would help in developing effective vaccine strategies.

d) In many cases tumor specific antigens found on avian tumors should be recognized by the chicken. This set of antigens has potential for understanding tumor regression in several avian systems.

Citations in the following list are incorporated by reference herein for the reasons cited.

REFERENCES

1. Purchase, H. G., C. Ludford, K. Nazerian, and H. W. Cox (1973). A new group of oncogenic viruses: reticuloendotheliosis, chick syncytial, duck infectious anemia, and spleen necrosis viruses. J. Natl. Cancer Inst., 51:489.
2. Mussman, H. C., and M. J. Twiehaus (1971). Pathogenesis of reticuloendothelial virus disease in chicks—an acute runting syndrome. Avian Dis., 15:483.
3. Olson, L. D. (1967). Histopathologic and hematologic changes in moribund stages of chicks infected with T-virus. Amer. J. Vet. Res., 28:1501.
4. Hoelzer, J. D., R. B. Franklin, and H. R. Bose (1979). Transformation by reticuloendotheliosis virus: development of a focus assay and isolation of a nontransforming virus. Virology, 93:20.
5. Temin, H. M., and V. K. Kassner (1974). Replication of reticuloendotheliosis viruses in cell culture: Acute infection. J. Virol., 13:291.
6. Witter, R. L., E. J. Smith, and L. B. Crittenden (1981). Tolerance, viral shedding, and neoplasia in chickens infected with non-defective reticuloendotheliosis viruses. Avian Dis., 25:374.
7. Witter, R. L., and L. B. Crittenden (1979). Lymphomas resembling lymphoid leukosis in chickens inoculated with reticuloendotheliosis virus. Int. J. Cancer., 23:673.
8. Noori-Daloii, M. R., R. A. Swift, and H-J. Kung (1981). Specific integration of REV proviruses in avian bursal lymphomas. Nature, 294:574.
9. Swift, R. A., E. Shaller, R. L. Witter, and H-J. Kung (1985). Insertional activation of c-myc by reticuloendotheliosis virus in chicken B lymphoma: Nonrandom distribution and orientation of the proviruses. J. Virol., 54:869.
10. Theilen, G. H., R. F. Zeigel, and M. J. Twiehaus (1966). Biological studies with RE virus (strain T) that induces reticuloendotheliosis in turkeys, chickens, and Japanese quail. J. Natl. Cancer Inst., 37:731.
11. Wong, T. C., and M. M. C. Lai (1981). Avian reticuloendotheliosis virus contains a new class of oncogene of turkey origin. Virology, 111:289.
12. Chen, I. S. Y., T. W. Mak, J. J. O'Rear, and H. M. Temin (1981). Characterization of reticuloendotheliosis virus strain T DNA and isolation of a novel variant of reticuloendotheliosis virus strain T by molecular cloning. J. Virol., 40:800.
13. Beug, H., H. Muller, S. Grieser, G. Doederlein, and T. Graf. (1981). Hematopoietic cells transformed in vitro by REV-T avian reticuloendotheliosis virus express characteristics of very immature lymphoid cells. Virology, 115:295.
14. Lewis, R. B., J. McClure, B. Rup, D. W. Niesel, R F. Garry, J. D. Hoelzer, K. Nazerian, and H. R. Bose (1981). Avian reticuloendotheliosis virus: Identification of the hematopoietic target cell for transformation. Cell, 25:421.
15. Shibuya, T., I. Chen, A. Howatson, and T. W. Mak. (1982). Morphological, immunological, and biochemical analyses of chicken spleen cells transformed in vitro by reticuloendotheliosis virus strain T. Cancer Res., 42:2722.
16. Keller, L. H., R. Rufner, and M. Sevoian (1979). Isolation and development of a reticuloendotheliosis virus-transformed lymphoblastoid cell line from chicken spleen cells. Infect. Immun., 25:694.
17. Rup, B. J., J. L. Spence, J. D. Hoelzer, R. B. Lewis, C. R. Carpenter, A. S. Rubin, and H. R. Bose (1979). Immunosuppression induced by avian reticuloendotheliosis virus: Mechanism of induction of the suppressor cell. J. Immunol., 123:1362.
18. Witter, R. L., L. F. Lee, L. D. Bacon, and E. J. Smith (1979). Depression of vaccinal immunity to Marek's disease by infection with reticuloendotheliosis virus. Infect. Immun., 26:90.
19. Franklin, R. B., R. L. Maldonado, and H. R. Bose (1974). Isolation and characterization of reticuloendotheliosis virus transformed bone marrow cells. Intervirol., 3:342.
20. Eskola, J., and P. Toivanen (1974). Effect of in vivo treatment with cyclophosphamide on lymphoid system in chicken. Cell. Immunol., 13:459.
21. Baba, T. W., and E. H. Humphries (1984). Avian leukcosis virus infection: Analysis of viremia and DNA integration in susceptible and resistant chicken lines. J. Virol., 51:123.
22. Hahn, E. C., L. Ramos, and A. J. Kenyon (1977). Lymphoproliferative diseases of fowl: JM-V leukemic lymphoblasts in cell culture: brief communication. J. Natl. Cancer Inst., 59:267.
23. Waite, M. R. F., and P. T. Allen (1975). RNA-directed DNA polymerase activity of reticuloendotheliosis virus: Characterization of the endogenous and exogenous reactions. J. Virol., 16:872.
24. Cui, Z-Z., L. F. Lee, R. F. Silva, and R. L. Witter (1986). Monoclonal antibodies against avian reticuloendotheliosis virus: identification of strain-specific and strain-common epitopes. J. Immunol., 136:4237.
25. Baba, T. W., and E. H. Humphries (1985). Formation of a transformed follicle is necessary but not sufficient for development of an avian leukosis virus-induced lymphoma. Proc. Natl. Aca. Sci. (USA)., 82:213.
26. Humphries, E. H., M. L. Danhof, and Hlozanek I (1984). Characterization of endogenous viral loci in five lines of white leghorn chickens. Virology., 135:125.
27. Wilhelmsen, K. C., and H. M. Temin (1984). Structure and dimorphism of c-rel (turkey), the cellular homolog to the oncogene of reticuloendotheliosis virus strain T. J. Virol., 49:521.
28. Taylor, H. W., and L. D. Olson (1973). Chronologic study of the T-virus in chicks. II. Development of hematologic changes. Avian Dis., 17:794.
29. DeBoer, G. F., H. J. L. Maas, J. Van Vloten, and J. E. Groenendal (1981). Horizontal transmission of lymphoid leukosis virus. Influence of age, maternal antibodies and degree of contact exposure. Avian Path., 10:343.
30. Crittenden, L. B., E. J. Smith, and A. M. Fadly (1984). Influence of endogenous viral gene expression and strain of exogenous avian leukosis virus (ALV) on mortality and ALV infection and shedding in chickens. Avian Dis., 28:1037.
31. Rice, N. R., R. R. Hiebsch, M. A. Gonda, H. R. Bose, and R. V. Gilden (1982). Genome of reticuloendotheliosis virus: Characterization by use of cloned proviral DNA. J. Virol., 42:237.
32. Chen, I. S. Y., K. C. Wilhelmsen, and H. M. Temin (1983). Structure and expression of c-rel, the cellular homolog to the oncogene of reticuloendotheliosis virus strain T. J. Virol., 45:104.
33. Rosenberg, N., and D. Baltimore (1978). The effect of helper virus on Abelson virus-induced transformation of lymphoid cells. J. Exp. Med., 147:1126.
34. Ruscetti, S., and L. Wolff (1985). Biological and biochemical differences between variants of spleen focus-forming virus can be localized to a region containing the 3' end of the envelope gene. J. Virol., 56:717.
35. Rup, B. J., J. D. Hoelzer, and H. R. Bose (1982). Helper viruses associated with avian acute leukemia viruses inhibit the cellular immune response. Virology, 116:61.
36. Baba, T. W., and E. H. Humphries (1986). Selective integration of avian leukosis virus in different hematopoietic tissues. Virology, 155:557.
37. Cianciolo, G. J., T. D. Copeland, S. Oroszlan, and R. Snyderman (1985). Inhibition of lymphocyte proliferation by a synthetic peptide homologous to retroviral envelope proteins. Science, 230:453.
38. Sonigo, P., C. Barker, E. Hunter, and S. Wain-Hobson (1986). Nucleotide sequence of Mason-Pfizer monkey virus: An immunosuppressive D-type retrovirus. Cell, 45:375.
39. Raschke, W. C., S. Baird, P. Ralph, and I. Nakoinz (1978). Functional macrophage cell lines transformed by Abelson leukemia virus. Cell, 15:261.
40. Waneck, G. L., and N. Rosenberg (1981). Abelson leukemia virus induces lymphoid and erythroid colonies in infected fetal cell cultures. Cell, 26:79.
41. Siden, E. J., D. Baltimore, D. Clark, and N. E. Rosenberg (1979). Immunoglobulin synthesis by lymphoid cells transformed in vitro by Abelson murine leukemia virus. Cell, 16:389.
42. Sklar, M. D., E. M. Shevach, I. Green, and M. Potter (1975). Transplantation and preliminary characterization of lymphocytic surface markers of Abelson virus-induced lymphomas. Nature, 253:550.
43. Premkumar, E., M. Potter, P. A. Singer, and M. D. Sklar (1975). Synthesis, surface deposition, and secretion of immunoglobulins by Abelson virus-transformed lymphosarcoma cell lines. Cell, 6:149.
44. Risser, R., M. Potter, and W. P. Rowe (1978). Abelson virus-induced lymphomagenesis in mice. J. Exp. Med., 148:714.
45. Hayward, W. S., B. G. Neel, and S. M. Astrin (1981). Activation of a cellular onc gene by promoter insertion in ALV-induced lymphoid leukosis. Nature, 290:475.

46. Payne, G. S., J. M. Bishop, and H. E. Varmus, (1982). Multiple arrangements of viral DNA and an activated host oncogene in bursal lymphomas. Nature, 295:209.

Changes may be made in the construction, operation and arrangement of the various parts, elements, steps and procedures described herein without departing from the concept and scope of the invention as defined in the following claims.

What is claimed is:

1. A method for preparing antibody-producing avian cell clones specific for a desired antigen, the method comprising:
   immunizing a bird with a desired antigen;
   separating a population of antibody-producing B-lymphocytes from said bird;
   treating said antibody-producing B-lymphocyte population in vitro with v-rel under conditions inducing transformation; and
   incubating said v-rel-treated B-lymphocyte population in vitro under conditions facilitating proliferation of antibody-producing B-lymphocytes transformed by v-rel.

2. A method of preparing antibody-producing avian cell clones specific for a desired antigen, the method comprising:
   immunizing a bird with a desired antigen;
   separating a population of antibody-producing B-lymphocytes from said bird;
   treating said antibody-producing lymphocyte population in vitro with reticuloendotheliosis virus and a non-cytotoxic avian helper virus to induce cell transformation; and
   incubating said treated B-lymphocyte population in vitro under conditions facilitating proliferation of transformed antibody-producing B-lymphocytes.

3. A method for preparing antibody-producing avian cell clones specific for a desired antigen, the method comprising:
   immunizing a first bird with a desired antigen;
   separating a population of antibody-producing B-lymphocytes from the first bird;
   treating said antibody-producing B-lymphocyte population in vitro with v-rel to produce transformed antibody-producing B-lymphocytes;
   transplanting said treated B-lymphocytes into a second bird, the second bird having been pretreated to remove normal B-lymphocytes, and allowing transformed B-lymphocytes to proliferate in the second bird; and
   isolating said transformed antibody-producing B-lymphocytes from the second bird.

4. The method of claim 1 or 2 wherein the incubating step comprises treatment of the treated B-lymphocyte population with the desired antigen and subsequent plating in microtiter plates.

5. The method of claim 1 or 2 wherein the incubating step comprises incubation of the treated B-lymphocyte population in culture medium comprising the desired antigen.

6. The method of claim 1 or 2 wherein the incubating step comprises incubation of the treated B-lymphocyte population in culture medium comprising B-cell mitogens.

7. The method of claim 6 wherein the B-cell mitogens are one or more of lectins, cytokines and antibodies directed against B-lymphocyte surface proteins.

8. The method of claims 1, 2, 3 wherein the separating involves panning said antibody-producing B-lymphocytes on solid surface comprising bound antibodies having binding specificity for avian IgM.

9. The method of claims 1, 2, 3 wherein the population of antibody-producing B-lymphocytes is separated from bursa, spleen, bone marrow, gland of Harder, intestinal lining or peripheral blood of the bird.

10. The method of claim 1 or 3 wherein the v-rel is included in a reticuloendotheliosis virus.

11. The method of claim 1, 2, 3 or wherein the bird is a chicken.

12. The method of claim 1 or 3 wherein the treating step involves transfection with a v-rel gene.

13. The method of claim 1 or 3 wherein the treating step involves electroporation.

14. The method of claim 1, 2, 3 or wherein the antibody produced is of an IgM isotype.

15. The method of claim 2 wherein the reticuloendotheliosis virus with a non-cytotoxic helper virus is REV-T(CSV).

16. The method of claim 2 wherein the helper virus is chick syncytial virus, spleen necrosis virus (SNV), attenuated REV-A or duck infectious anemia virus (DIAV).

17. The method of claim 1 or 2 wherein the incubating step involves plating cells out in microtiter plates.

18. The method of claim 1 or 2 wherein the incubating step involves cell culturing in microtiter plates for a period of at least about one week.

19. The method of claim 1 or 2 wherein the bird is between about six weeks and two years of age.

20. The method of claim 1, 2, 3 or wherein the immunization is monitored by routine serological analysis.

21. The method of claim 1, 2, 3 or wherein the immunization is indicated by measurement of an antibody titer greater than about 1/200.

22. The method of claim 1, 2, 3 or wherein the separation of antibody-producing B-lymphocytes involves centrifugation in a density gradient comprising polysaccharide.

23. The method of claim 1 or 2 wherein an isolating step involving plating out transformed B-lymphocytes, follows the incubating step.

24. The method of claim 1 or 2 wherein an isolating step involving selecting cell clones producing antibody directed against the desired antigen, follows the incubating step.

25. The method of claim 1 or 2 wherein an isolating step involving panning said transformed B-lymphocytes on a solid surface comprising a bound second antibody having a specific binding specificity for an avian antibody, follows the incubating step.

* * * * *